(12) United States Patent
Chapoulaud

(10) Patent No.: US 7,702,172 B2
(45) Date of Patent: Apr. 20, 2010

(54) PARTICLE EXTRACTION FOR AUTOMATIC FLOW MICROSCOPE

(75) Inventor: Eric Chapoulaud, Pasadena, CA (US)

(73) Assignee: IRIS International, Inc., Chatsworth, CA (US)

( * ) Notice: Subject to any disclaimer, the term of this patent is extended or adjusted under 35 U.S.C. 154(b) by 1776 days.

(21) Appl. No.: 10/716,253

(22) Filed: Nov. 17, 2003

(65) Prior Publication Data

US 2004/0136593 A1 Jul. 15, 2004

Related U.S. Application Data

(60) Provisional application No. 60/427,466, filed on Nov. 18, 2002.

(51) Int. Cl.
*G06K 9/42* (2006.01)
(52) U.S. Cl. .................. 382/256; 382/199; 382/278
(58) Field of Classification Search ............ 382/199, 382/256
See application file for complete search history.

(56) References Cited

U.S. PATENT DOCUMENTS

| | | | |
|---|---|---|---|
| 4,338,024 A | 7/1982 | Bolz et al. | |
| 4,393,466 A | 7/1983 | Deindoerfer et al. | |
| 4,538,299 A * | 8/1985 | DeForest | 382/197 |
| 4,612,614 A | 9/1986 | Deindoerfer et al. | |
| 5,600,761 A | 2/1997 | Ng et al. | |
| 5,625,709 A | 4/1997 | Kasdan | |
| 5,640,468 A * | 6/1997 | Hsu | 382/190 |
| 6,269,194 B1 | 7/2001 | Nichani | |
| 6,272,253 B1 | 8/2001 | Bannon et al. | |
| 6,289,126 B1 * | 9/2001 | Ishisaka | 382/205 |
| 6,400,846 B1 * | 6/2002 | Lin et al. | 382/199 |
| 6,516,097 B1 * | 2/2003 | Pritt | 382/256 |
| 7,020,335 B1 * | 3/2006 | Abousleman | 382/199 |
| 7,031,525 B2 * | 4/2006 | Beardsley | 382/199 |
| 7,110,602 B2 * | 9/2006 | Krause | 382/199 |
| 7,142,600 B1 * | 11/2006 | Schonfeld et al. | 375/240.16 |
| 7,236,623 B2 * | 6/2007 | Chapoulaud et al. | 382/133 |
| 2002/0031255 A1 * | 3/2002 | Kasdan et al. | 382/156 |

OTHER PUBLICATIONS

F.Schaffalizky, A.Zisserman, Multi-view matching for unordered image sets, or "How do I organize my holiday snaps?", May 28-31, 2002, vol. 2350/2002, pp. 1-17.*

F.Schaffalizky, A.Zisserman, Multi-view matching for unordred image sets, or "How do I organize my holidy snaps", May 28-31, 2002, vol. 2350/2002, pp. 1-17.*

* cited by examiner

*Primary Examiner*—Daniel G Mariam
*Assistant Examiner*—Aklilu k Woldemariam
(74) *Attorney, Agent, or Firm*—DLA Piper LLP

(57) ABSTRACT

A method and apparatus for locating the boundary of an object. An electronic image of the object is formed, having a plurality of image pixels. Groups of the image pixels are identified that represent edge segments of the object. Patches are formed around the image pixel groups, where each patch is dimensioned and positioned to entirely contain one of the image pixel groups. A patch merge process is preformed that merges any two of the patches together that overlap each other by a predetermined amount, to form a merged patch that is dimensioned and positioned to entirely contain the two merged patches. The merge process continues for any overlapping patches and merged patches until none of the patches and the merged patches overlap each other by the predetermined amount. All the edge segments contained within one of the merged patches are associated as representing the boundary of the object.

38 Claims, 5 Drawing Sheets

PARTICLE EXTRACTION FOR AUTOMATIC FLOW MICROSCOPE

This application claims the benefit of U.S. Provisional Application No. 60/427,466, filed Nov. 18, 2002.

FIELD OF THE INVENTION

The present invention relates to methods and systems for analyzing particles in a dilute fluid sample, and more particularly to a method and apparatus for automatically locating the boundary of an object in a field of view.

BACKGROUND OF THE INVENTION

Methods and systems for analyzing particles in a dilute fluid sample are well known, as disclosed in U.S. Pat. Nos. 4,338,024 and 4,393,466. Existing flow microscope particle analyzers use an image acquisition device and software that detects particles based on their brightness difference with the background. U.S. Pat. Nos. 4,538,299 and 5,625,709 are examples of such analyzers. Unfortunately, currently employed systems and methods often cannot efficiently detect low contrast particles, and often identify different parts of the same object as different objects, resulting in incorrect classification and reported element quantity.

SUMMARY OF THE INVENTION

The present invention is a method of accurately identifying particle images, and producing image segments each containing the image of a single particle.

The present invention is a method for automatically locating a boundary of an object of interest in a field of view, which includes forming an electronic image of the field of view containing the object, wherein the electronic image is formed of a plurality of image pixels, identifying groups of the image pixels that represent edge segments of the object, forming patches around the image pixel groups, wherein each patch is dimensioned and positioned to entirely contain one of the image pixel groups, and performing a patch merge process that merges any two of the patches together that meet a predetermined proximity threshold relative to each other to form a merged patch that is dimensioned and positioned to entirely contain the two merged patches. The merge process continues for any of the patches and the merged patches meeting the predetermined proximity threshold until none of the patches and the merged patches meet the predetermined proximity threshold.

The present invention is also an apparatus for automatically locating a boundary of an object of interest in a field of view, which includes an imaging system for forming an electrical image of the field of view containing the object, wherein the electronic image is formed of a plurality of image pixels, and at least one processor. The at least one processor identifies groups of the image pixels that represent edge segments of the object, forms patches around the image pixel groups, wherein each patch is dimensioned and positioned to entirely contain one of the image pixel groups, and performs a patch merge process that merges any two of the patches together that meet a predetermined proximity threshold relative to each other to form a merged patch that is dimensioned and positioned to entirely contain the two merged patches. The merge process continues for any of the patches and the merged patches meeting the predetermined proximity threshold until none of the patches and the merged patches meet the predetermined proximity threshold.

Other objects and features of the present invention will become apparent by a review of the specification, claims and appended figures.

BRIEF DESCRIPTION OF THE DRAWINGS

FIG. 5 is an example of a pixel value array for an exemplary binary image derived from method steps of FIG. 4.

FIG. 6 is an example of the pixel value array of FIG. 5 after edge detection.

FIG. 7 is an example of the pixel value array of FIG. 6 after the formation of patches.

FIGS. 8A-8C are examples of the pixel value array of FIG. 7 illustrating the merging of patches around a single particle.

DETAILED DESCRIPTION OF THE PREFERRED EMBODIMENTS

Figure 1:
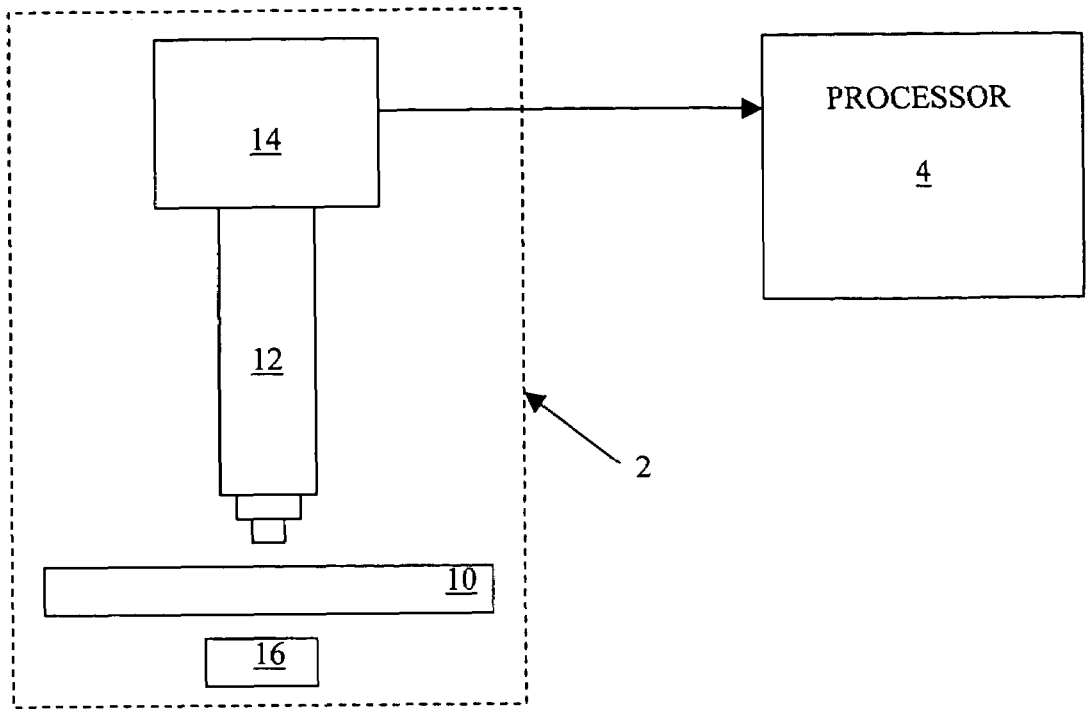
FIG. 1 is a schematic diagram of a particle analyzer employing the method of the present invention.

The method of the present invention enhances the detection of particles to allow low contrast particle detection and object parts combination. The method includes 5 basic steps, and can be employed using a conventional particle analyzer having an imaging system 2 and a processor 4, as schematically illustrated in FIG. 1.

Imaging System and Processor

Imaging system 2 is used to produce images of fields of view of a sample containing the particles of interest. Imaging system 2 is preferably a well known flow microscope as described in U.S. Pat. Nos. 4,338,024, 4,393,466, 4,538,299 and 4,612,614, which are all hereby incorporated herein by reference. Such systems include a flow cell 10, a microscope 12, and a camera 14, as shown in FIG. 1. Specimen fluid containing the particles of interest is passed through an examination area of the flow cell 10, whereby images of the particles are viewable through the flow microscope 12. The camera 14 (which is preferably a CCD camera) captures images of successive fields of view of the particles via the microscope 12, as the particles flow through the flow cell 10, and converts them to digital particle images. Each of the digital particle images taken by the camera 14 comprise thousands or even millions of individual pixels. A light source 16 (e.g. strobe) is preferably used to illuminate (by front and/or back lighting) the examination area of the flow cell 10. It should be noted that the present invention can also be applied to an imaging system that analyzes non-flowing specimen fluid (e.g. specimen fluid placed on an examination slide).

Processor 4 can be any microprocessor and/or computer system, or a plurality of microprocessors and/or computer systems, capable of processing the digital particle images as described below. Examples of such processors include, but are not limited to, data processors, DSP's (digital signal processors), microcontrollers, and computer system processors, each of which can be CISC and/or RISC type.

Method of Particle Detection Enhancement

Figure 2:
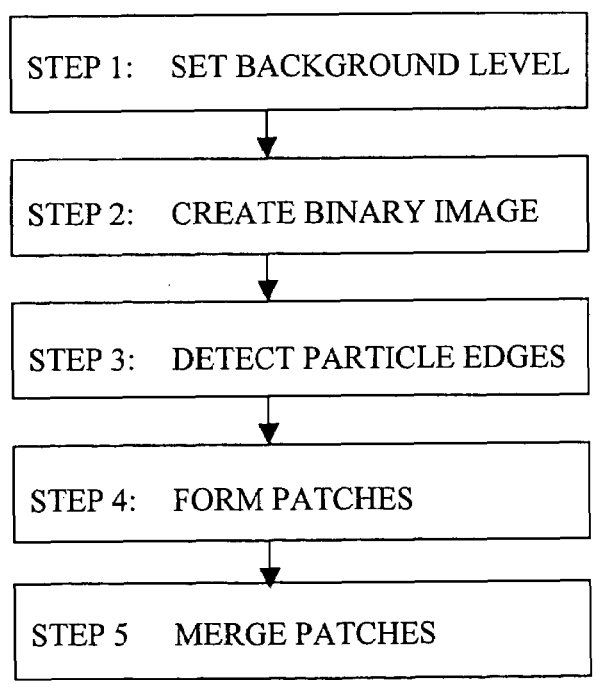
FIG. 2 is a flow chart showing the method steps of the present invention.

There are five basic steps of the particle detection method of the present invention, as illustrated in FIG. 2: 1) Setting Background Level, 2) Creating Binary Image, 3) Detecting Particle Edges, 4) Forming Patches, and 5) Merging Patches.

Step 1: Setting Background Level

Figure 3:
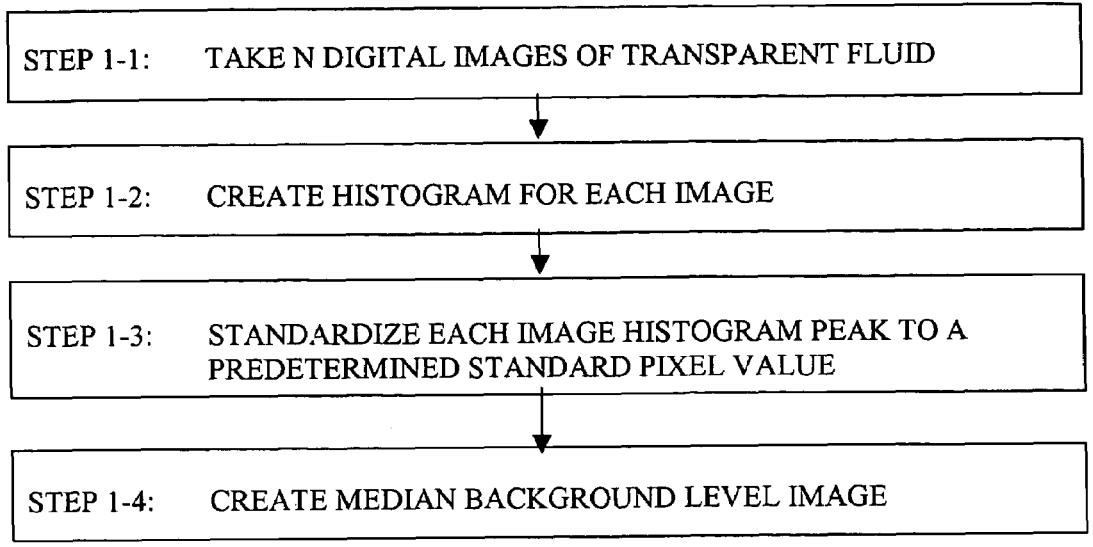
FIG. 3 is a flow chart showing the method steps for setting the background level.

FIG. 3 illustrates the four steps of setting a background level. This process not only creates a median background level for each pixel location, but does so in a manner that compensates for any fluctuations in the background illumination from image to image (e.g. different intensities from strobe 16 which can adversely affect the resulting accuracy of the system).

First (in step 1-1), a transparent fluid is sent through the flow cell 10 (or placed on examination slides), where N images of the transparent fluid are taken by camera 14 and digitized to create N digitized background images. As a non-limiting example, N can equal 3. Second (in step 1-2), histograms of the digital background image pixel values are made for each of the N images, where the peak value of each histogram corresponds to an average pixel value for that image. Third (in step 1-3), a predetermined "standardization" pixel value is selected, and each image is standardized to that pixel value by adding to or subtracting from all its pixel values, so that all of the N images have a histogram peak at the predetermined standardization pixel value. For example, if the predetermined standardization pixel value is 215, and one of the N images has a histogram peak at 210, then all pixels in that image are increased by a value of 5. If another of the N images has a histogram peak at 190, then all pixel values in that image are increased by 25. Thus, all N images are standardized to a single pixel value, which compensates for fluctuations in background illumination from image to image. Fourth (in step 1-4), for each pixel location of the digital images, a median pixel value is determined from the pixel values in all of the N images (as corrected by the standardization step 1-3), where a median background level image is created on a pixel location by pixel location basis. Thus, each pixel value of the median background level image represents the corrected median value for that pixel location from all of the standardized N images, where N can be any number of images, including 1.

Preferably, the predetermined standardization pixel value is selected to be as high as possible without causing pixel saturation. Thus, in a system where the pixel values can range from 0 to 255, the predetermined standardization pixel value is selected to prevent any of pixel values in the background images from reaching 255.

By compensating for background illumination (e.g. flash to flash) variations, it allows the system to operate with a lower threshold for distinguishing between background pixels and pixels that accurately reflect the particle edges, as discussed further below. It should be noted that for systems having minimal background illumination fluctuations from image to image, the illumination compensation of steps 1-2 and 1-3 can be omitted, whereby the median background level image is calculated in step 1-4 directly from measured pixel values of the N images taken in step 1-1 (without any standardization thereof), even where N equal 1. If N equals 1, then the median pixel values are the measured pixel values.

Step 2: Binary Image Creation

Figure 4:
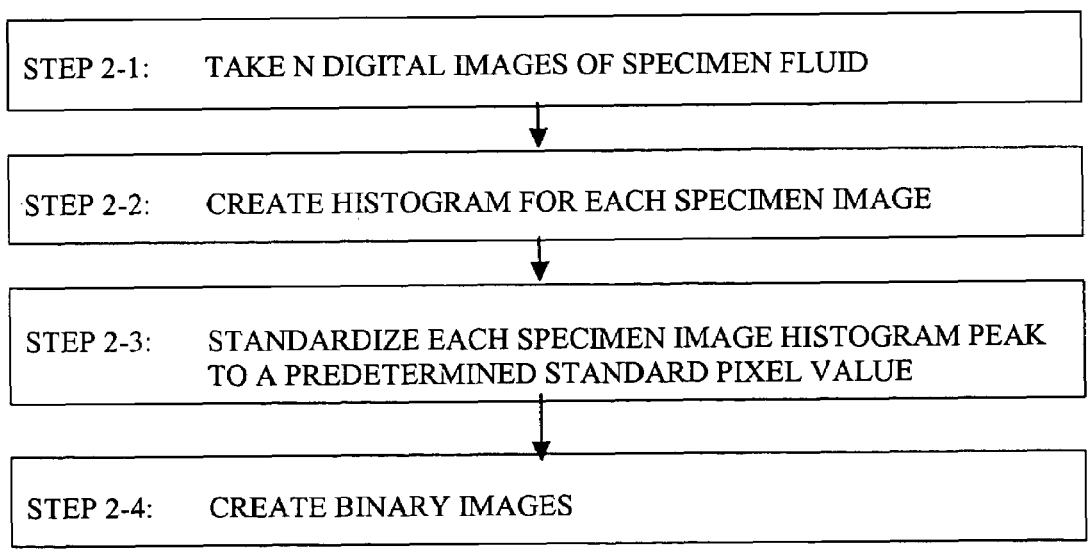
FIG. 4 is a flow chart showing the method steps for creating binary images.

FIG. 4 illustrates the steps for creating binary images. First (step 2-1), specimen fluid containing the particles of interest is sent through the flow cell (or positioned on examination slides), where images of the specimen fluid (and the particles therein) are taken by the camera 14 and digitized to form digital specimen images. Preferably but not necessarily, the illumination compensation discussed above (steps 1-2 and 1-3) is performed on each of the specimen images (to compensate for illumination differences from specimen image to specimen image). Specifically, histograms of the pixel values are made for each of the specimen images, where the peak value of each histogram corresponds to an average pixel value for that specimen image (step 2-2). A predetermined standardization pixel value is selected (preferably using the highest value possible while avoiding pixel saturation), and each specimen image is standardized to that pixel value by adding to or subtracting from all its pixel values as described above, so that all of the specimen images have a histogram peak at the predetermined standardization pixel value (step 2-3). Preferably, the predetermined standardization pixel value for the specimen image is the same as that used for standardizing the background images. Finally, a binary image is created for each specimen image on a pixel by pixel basis (step 2-4), which highlights only those pixels for which the difference between the median background level image value and the specimen image value exceeds a predetermined threshold value X.

Figures 5, 6:
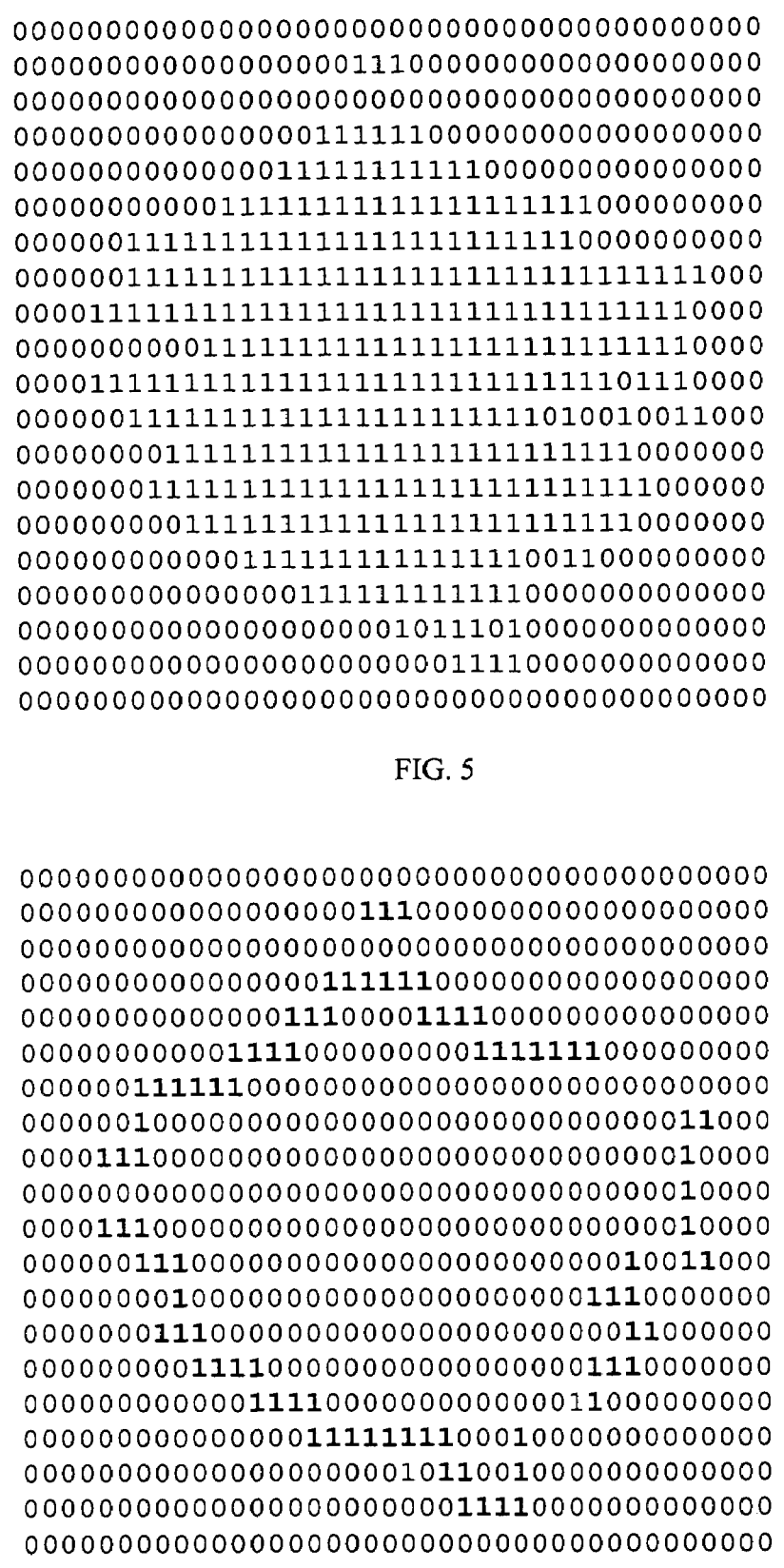

FIG. 5 illustrates an example of a binary image, where the binary image pixel values are assigned one value (e.g. a "1") where the difference between corresponding specimen image pixel values and median background level image pixel values exceed the threshold value X, with the remaining binary image pixels assigned a second pixel value (e.g. a "0"). It should be noted that for specimen images that are backlit, pixels corresponding to the background are lighter (have a greater intensity value) than those pixels corresponding to portions of the particles.

The predetermined threshold value X is selected to be as small as possible, without incurring too much noise, to maximize the sensitivity of the system for low contrast particle images. If the threshold is set too high, the system will erroneously identify, as part of the background, some pixels that in fact correspond to portions of the particles. If the threshold is set too low, the system will erroneously identify, as part of the particles, some pixels that in fact correspond to portions of the background. For best results, the ideal threshold value X should be empirically determined for each system.

Step 3: Edge Detection

For each of the specimen images, edges of the various particles therein are determined using the corresponding binary image created in Step 3. Particle edge detection in imaging systems is well known, and involves the process of identifying those pixels of the specimen images that correspond to the edges of the particles in those images. For example, pixels corresponding to the particle edges are often identified as those having neighboring pixels on one side that correspond to the image's background, and having neighboring pixels on the other side that correspond to the particle interior. Typical edge detection techniques start by identifying one or more edge pixels, and then search for more such edge pixels adjacent those already so identified. Exemplary particle edge tracing techniques are disclosed in U.S. Pat. Nos. 5,626,709 and 4,538,299, which are incorporated herein by reference. Once the edge pixels are identified, those pixels are distinguished from the rest of the image (which corresponds to background and particle interior portions of the image). For example, the binary image of FIG. 5 can be processed using an edge detection technique such that those pixels that are identified as edge pixels are left assigned as "1's", with the remaining pixels all assigned as "0's", as illustrated in FIG. 6. The result is a plurality of pixels that define particle edges or edge segments (an edge segment is formed by a group of edge pixels that continuously define at least a portion of a particle edge).

Step 4: Patch Formation

Figures 7, 8A:
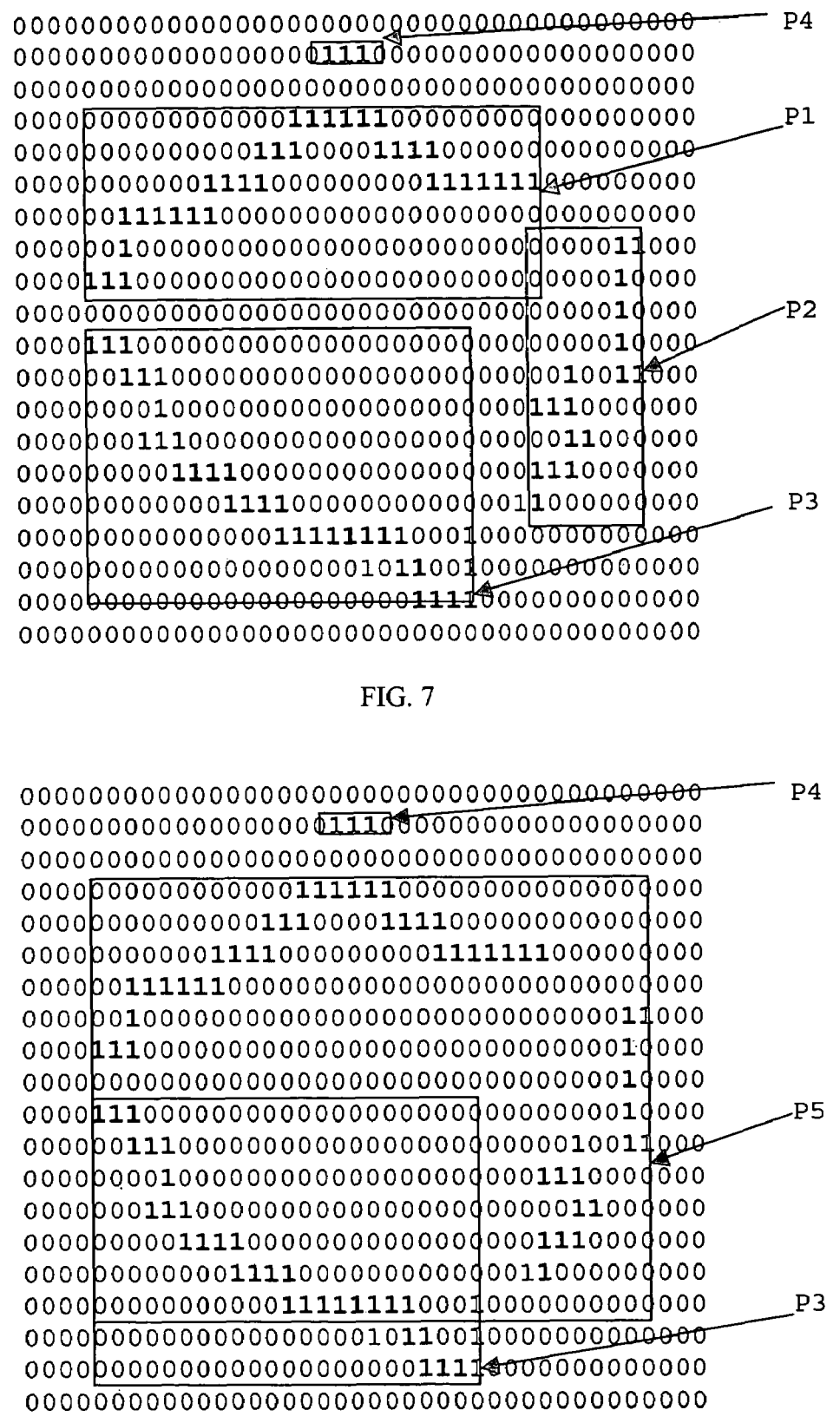

For each specimen image, rectangular patches are created around each detected particle edge or edge segment, where each patch is dimensioned as small as possible while still containing the entire detected particle edge or edge segment. A simple exemplary creation of the rectangular patches for the binary image of FIG. 6 is illustrated in FIG. 7, where four distinct edge segments for one particle result in four rectangular patches (P1, P2, P3 and P4).

As an optional step, each patch can be enlarged by expanding each of its walls away from the patch center by the same predetermined amount. For example, if a patch size is 10×20 pixels, and the predetermined amount is 5 pixels, then each patch wall is moved back by 5 pixels, leaving a patch size of 20×30. The optimal predetermined amount of enlargement, which produces the most accurate particle identification results, will vary depending on system design, and can be empirically determined. In a particle analyzer that has been reduced to practice, the optimal predetermined amount of enlargement was determined by trial and error to be 12 pixels (out of approximately 1.4 million total pixels in the entire image), such that a patch size of 10×20 is expanded to a patch size of 34×44. The patches are preferably enlarged before proceeding to the fifth and final step.

Step 5: Patch Merge

The final step is to successively merge overlapping patches to identify those patches (and the edge segments therein) that belong to the same particle. The merge process begins by merging together any of the patches created (and possibly expanded) from Step 4 that overlap each other by sharing more than a predetermined number of pixels Y. Thus, for any two patches that meet that criteria, the two patches are merged into a single patch, where the single patch represents the smallest rectangle that can entirely contain both of the overlapping patches. This merging process continues using the original patches from Step 4, the merged patches of the present step, and/or any combinations of the two, until no further patches can be merged using the above described criteria.

Figures 8B, 8C:
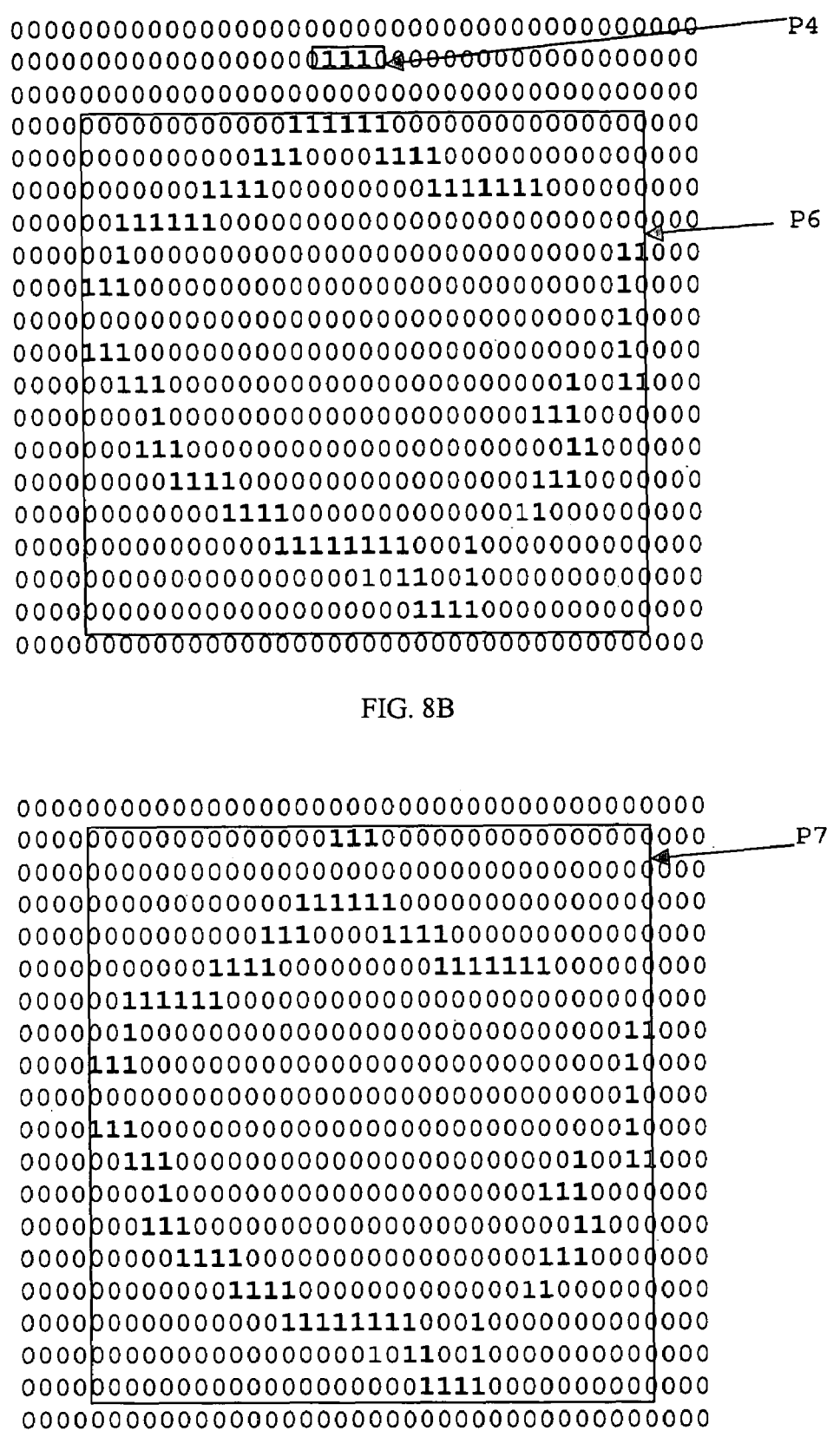

FIGS. 8A to 8C illustrate a simplistic example of the merging of patches from FIG. 7. In FIG. 7, two of the patches (P1 and P2) are overlapping (by having two pixels in common). Assuming the predetermined number of pixels Y does not exceed two, patches P1 and P2 are merged together as shown in FIG. 8A into a single merged patch P5. Patch P5 now overlaps with patch P3, where FIG. 8B illustrates the merger of patches P5 and P3 to result in merged patch P6. In this particular example, no more merging takes place, because patch P6 does not overlap patch P4. FIG. 8B is a good example of why the optional patch enlargement step should be utilized, as it ensures patches adjacent but distinct from the other patches from the same particle are included in the final merged patch. Had patch enlargement of just a single pixel been performed before or even during the patch merge process, all four of the original patches (P1, P2, P3, P4) that represent four distinct particle edge segments of the same particle would have been properly included in the final merged patch P7, as illustrated in FIG. 8C.

Once patch merging is complete, those edge segments found within one of the final patches are associated with a single particle (as representing the boundary of that single particle), and any edge segment(s) found outside of that final patch are associated as either non-particles or part of an adjacent but distinct particle. At this time, any gaps between the edge segments within the one final patch can be filled in to form a single and continuous particle edge.

The optimal value of the predetermined number of pixels Y required to merge two patches will vary from system to system, and can be empirically determined. In a particle analyzer that has been reduced to practice, 50 pixels (out of 1.4 million total pixels in the entire image) was found to be an optimal predetermined number Y of shared pixels for triggering a merging of overlapping patches. Once the patch merge process is completed, then each remaining patch should contain no more than the image of a single particle.

By isolating each particle in distinct and known patches, the system can reliably avoid identifying different parts of the same particle as different particles, whereby any gaps in the particle edges can be filled in within each patch without the risk of bridging an edge portion of one particle to an edge portion of another particle.

Patching merging as described above and illustrated in the drawings are described with respect to overlapping boundaries of the patches. However, patch merging can be performed in any manner that measures a proximity of the patches, where patches are merged if they meet a particular proximity threshold. Proximity can be measured simply by the overlap of patch boundaries containing distinct particle edge segments, as illustrated and described above. But in addition, other measures of proximity could be used, such as a measured distance or distances between patch boundary portions (e.g. distance between closest patch boundary portions, distance between furthest patch boundary portions, etc.), or a gravitational-like attraction criteria based on both patch sizes and separation distance(s) (e.g. consider overall size of patches and distance between patch centers, which is analogous to a mass and gravitational force analysis), where "big" patches might merge, but big and small patches with similar separation may not. Thus, the proximity threshold could be a particular number of pixels shared by two overlapping patches, or could be distance(s) between boundary segments of two patches, or could be a value based upon the sizes of the patches divided by the distance between the patch boundaries or the patch centers.

It is to be understood that the present invention is not limited to the embodiment(s) described above and illustrated herein, but encompasses any and all variations falling within the scope of the appended claims. For example, as is apparent from the claims and specification, not all method steps need be performed in the exact order illustrated or claimed, but rather in any order that allows the proper isolation of particles in separate and distinct patches. Further, the shape of the patches need not necessarily be rectangular, and can vary in shape and orientation to optimize their merging behavior. Some shapes such as rectangles would more aggressively "capture" adjacent patches, while other shapes such as circles and ovals would minimize capture of adjacent objects, assuming that all objects were inherently convex. In addition, while the system preferably automatically associates all the edge segments contained within the merged patch as representing the boundary of the object, it need not necessarily do so. Instead, the resulting edge segments contained with the merged patch can simply be presented to the user for analysis, or be used by the system for other analysis purposes.

What is claimed is:

1. A method for automatically locating a boundary of an object of interest in a field of view, the method comprising:
forming an electronic image of the field of view containing the object using an imaging system, wherein the electronic image is formed of a plurality of image pixels;
identifying groups of the image pixels that represent edge segments of the object using at least one processor;
forming patches around the image pixel groups using the at least one processor, wherein each patch is dimensioned and positioned to entirely contain one of the image pixel groups; and
performing a patch merge process using the at least one processor that merges any two of the patches together that meet a predetermined proximity threshold relative to each other to form a merged patch that is dimensioned and positioned to entirely contain the two merged patches, wherein the merge process continues for any of the patches and the merged patches meeting the predetermined proximity threshold until none of the patches and the merged patches meet the predetermined proximity threshold.

2. The method of claim 1, further comprising:
associating all the edge segments contained within one of the merged patches as representing the boundary of the object using the at least one processor.

3. The method of claim 1, wherein the predetermined proximity threshold is a predetermined number of the image pixels shared by any of the patches and merged patches that overlap each other.

4. The method of claim 1, wherein the predetermined proximity threshold is a predetermined distance between any of the patches and merged patches.

5. The method of claim 4, wherein the predetermined distance is measured from boundaries of the patches and merged patches.

6. The method of claim 4, wherein the predetermined distance is measured from center portions of the patches and merged patches.

7. The method of claim 1, wherein the predetermined proximity threshold is calculated from the sizes and separation distances of the patches and merged patches.

8. The method of claim 1, wherein the forming of the patches further comprises:
dimensioning each of the patches as small as possible while still entirely containing one of the image pixel groups.

9. The method of claim 8, wherein after the dimensioning of the patches as small as possible, the forming of the patches further comprises:
expanding each of the patches by moving wall portions of the patch away from a center of the patch by a predetermined distance.

10. The method of claim 9, wherein each of the patches has a rectangular shape.

11. The method of claim 1, wherein the identifying of the groups of image pixels that represent edge segments of the object comprises:
forming a background level image of the field of view, wherein the background level image is formed of a plurality of background level pixels each corresponding in location to one of the image pixels and each having a pixel value;
classifying as an object pixel each of the image pixels having a pixel value that varies by at least a predetermined amount from the pixel value of the corresponding background level pixel; and
identifying which of the object pixels correspond to an edge of the object.

12. The method of claim 11, wherein the forming of the background level image of the field of view further comprises:
forming N background electronic images of the field of view not containing any objects of interest, wherein each of the background electronic images is formed of a plurality of background pixels each corresponding in location to one of the background level pixels and each having a pixel value, and wherein N is a positive integer; and
generating each one of the background level pixels by calculating a median value of the pixel values for the background pixels corresponding to the one background level pixel.

13. The method of claim 12, wherein the formation of the N background electronic images of the field of view includes flowing transparent fluid through the field of view.

14. The method of claim 12, wherein the forming of the background level image of the field of view further comprises:
standardizing average values of the background pixel values for each of the N background electronic images before the generation of the background level pixels.

15. The method of claim 14, wherein the standardizing average values of the background pixel values further comprises:
creating a histogram for each one of the N background electronic images, wherein each of the histograms has a peak value that corresponds to an average value of the background pixel values for one of the N background electronic images;
selecting a predetermined average pixel value; and
adjusting the background pixel values for the N background electronic images so that the histograms thereof all have peak values generally equal to the predetermined average pixel value.

16. The method of claim 15, wherein the predetermined average pixel value is selected such that the adjusted background pixel values do not exceed a maximum pixel value thereof.

17. The method of claim 11, wherein the classifying as an object pixel further includes:
creating a binary image of the electronic image of the field of view containing the object, wherein the binary image is formed of a plurality of binary pixels each corresponding in location to one of the image pixels, wherein each of the binary pixels is assigned to a first value if the corresponding image pixel value varies by at least a predetermined amount from the pixel value of the corresponding background level pixel, and is assigned to a second value if the corresponding image pixel value does not vary by at least the predetermined amount from the pixel value of the corresponding background level pixel.

18. The method of claim 17, wherein the identifying which of the object pixels correspond to an edge of the object includes:
re-assigning any of the binary pixels assigned with the first value to the second value that are surrounded by others of the binary pixels all originally assigned with the first value.

19. The method of claim 1, wherein each of image pixels has a value, and wherein the forming of the electronic image of the field of view containing the object further comprises:

creating a histogram for the electronic image containing the object, wherein the histogram has a peak value that corresponds to an average value of the image pixel values;

selecting a predetermined average pixel value; and adjusting the image pixel values so that the histogram has a peak value generally equal to the predetermined average pixel value.

20. An apparatus for automatically locating a boundary of an object of interest in a field of view, comprising:

an imaging system for forming an electrical image of the field of view containing the object, wherein the electronic image is formed of a plurality of image pixels;

at least one processor for:

identifying groups of the image pixels that represent edge segments of the object, forming patches around the image pixel groups, wherein each patch is dimensioned and positioned to entirely contain one of the image pixel groups, and performing a patch merge process that merges any two of the patches together that meet a predetermined proximity threshold relative to each other to form a merged patch that is dimensioned and positioned to entirely contain the two merged patches, wherein the merge process continues for any of the patches and the merged patches meeting the predetermined proximity threshold until none of the patches and the merged patches meet the predetermined proximity threshold.

21. The apparatus of claim 20, wherein the at least one processor associates all the edge segments contained within one of the merged patches as representing the boundary of the object.

22. The apparatus of claim 20, wherein the predetermined proximity threshold is a predetermined number of the image pixels shared by any of the patches and merged patches that overlap each other.

23. The apparatus of claim 20, wherein the predetermined proximity threshold is a predetermined distance between any of the patches and merged patches.

24. The apparatus of claim 23, wherein the predetermined distance is measured from boundaries of the patches and merged patches.

25. The apparatus of claim 24, wherein the predetermined distance is measured from center portions of the patches and merged patches.

26. The apparatus of claim 20, wherein the predetermined proximity threshold is calculated from the sizes and separation distances of the patches and merged patches.

27. The apparatus of claim 20, wherein the forming of the patches by the at least one processor further comprises:

dimensioning each of the patches as small as possible while still entirely containing one of the image pixel groups.

28. The apparatus of claim 27, wherein after the dimensioning of the patches as small as possible, the forming of the patches by the at least one processor further comprises:

expanding each of the patches by moving wall portions of the patch away from a center of the patch by a predetermined distance.

29. The apparatus of claim 28, wherein each of the patches has a rectangular shape.

30. The apparatus of claim 20, wherein the groups of image pixels that represent edge segments of the object are identified by the at least one processor by:

forming a background level image of the field of view, wherein the background level image is formed of a plurality of background level pixels each corresponding in location to one of the image pixels and each having a pixel value;

classifying as an object pixel each of the image pixels having a pixel value that varies by at least a predetermined amount from the pixel value of the corresponding background level pixel; and identifying which of the object pixels correspond to an edge of the object.

31. The apparatus of claim 30, wherein the system forms the background level image of the field of view by:

forming N background electronic images of the field of view not containing any objects of interest, wherein each of the background electronic images is formed of a plurality of background pixels each corresponding in location to one of the background level pixels and each having a pixel value, and wherein N is a positive integer; and generating each one of the background level pixels by calculating a median value of the pixel values for the background pixels corresponding to the one background level pixel.

32. The apparatus of claim 31, wherein the system flows transparent fluid through the field of view to form the N background electronic images of the field of view.

33. The apparatus of claim 31, wherein the at least one processor forms of the background level image of the field of view by:

standardizing average values of the background pixel values for each of the N background electronic images before the generation of the background level pixels.

34. The apparatus of claim 33, wherein the at least one processor standardizes the average values of the background pixel values by:

creating a histogram for each one of the N background electronic images, wherein each of the histograms has a peak value that corresponds to an average value of the background pixel values for one of the N background electronic images;

selecting a predetermined average pixel value; and adjusting the background pixel values for the N background electronic images so that the histograms thereof all have peak values generally equal to the predetermined average pixel value.

35. The apparatus of claim 34, wherein the at least one processor selects the predetermined average pixel value such that the adjusted background pixel values do not exceed a maximum pixel value thereof.

36. The apparatus of claim 30, wherein the at least one processor classifies the object pixels by:

creating a binary image of the electronic image of the field of view containing the object, wherein the binary image is formed of a plurality of binary pixels each corresponding in location to one of the image pixels, wherein each of the binary pixels is assigned to a first value if the corresponding image pixel value varies by at least a predetermined amount from the pixel value of the corresponding background level pixel, and is assigned to a second value if the corresponding image pixel value does not vary by at least the predetermined amount from the pixel value of the corresponding background level pixel.

37. The apparatus of claim 36, wherein the at least one processor identifies which of the object pixels correspond to an edge of the object by:

re-assigning any of the binary pixels assigned with the first value to the second value that are surrounded by others of the binary pixels all originally assigned with the first value.

38. The apparatus of claim 20, wherein each of image pixels has a value, and wherein the at least one processor forms the electronic image of the field of view containing the object further by:

creating a histogram for the electronic image containing the object, wherein the histogram has a peak value that corresponds to an average value of the image pixel values;

selecting a predetermined average pixel value; and adjusting the image pixel values so that the histogram has a peak value generally equal to the predetermined average pixel value.

* * * * *